US011262021B2

(12) United States Patent
Daugirdas et al.

(10) Patent No.: US 11,262,021 B2
(45) Date of Patent: Mar. 1, 2022

(54) METHODS AND SYSTEMS FOR A PIVOTABLE TABLET MOUNT

(71) Applicant: General Electric Company, Schenectady, NY (US)

(72) Inventors: Kristofer Daugirdas, Salt Lake City, UT (US); Naveen Stephan Chandra, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 350 days.

(21) Appl. No.: 16/198,719

(22) Filed: Nov. 21, 2018

(65) Prior Publication Data

US 2020/0158278 A1 May 21, 2020

(51) Int. Cl.
*F16M 13/02* (2006.01)
*A61B 6/00* (2006.01)

(52) U.S. Cl.
CPC ........... *F16M 13/02* (2013.01); *A61B 6/4405* (2013.01); *A61B 6/4441* (2013.01); *F16M 2200/022* (2013.01); *F16M 2200/024* (2013.01); *F16M 2200/06* (2013.01)

(58) Field of Classification Search
None
See application file for complete search history.

(56) References Cited

U.S. PATENT DOCUMENTS

| 2003/0075649 | A1* | 4/2003 | Jeong | F16M 11/2064 248/157 |
| 2010/0108833 | A1* | 5/2010 | Long | F16M 11/30 248/188.6 |
| 2011/0075350 | A1* | 3/2011 | Lindblad | F16M 11/2021 361/679.41 |
| 2014/0054431 | A1* | 2/2014 | Hung | F16M 13/027 248/324 |
| 2015/0146847 | A1 | 5/2015 | Liu | |
| 2015/0211675 | A1 | 7/2015 | Shyu | |
| 2016/0296185 | A1 | 10/2016 | Gemmel et al. | |
| 2018/0292028 | A1* | 10/2018 | Gossack | F16G 11/101 |

FOREIGN PATENT DOCUMENTS

| DE | 102015218919 A1 | 3/2017 |
| JP | 2006326298 A | 12/2006 |
| TW | 201328356 A | 7/2013 |

OTHER PUBLICATIONS

Daugirdas, K. et al., "An Ornamental Design for a Display Screen Mount," U.S. Appl. No. 29/671,089, filed Nov. 21, 2018, 23 pages.
(Continued)

*Primary Examiner* — Hoon K Song
(74) *Attorney, Agent, or Firm* — McCoy Russell LLP

(57) ABSTRACT

A system for mounting a medical imaging device on a tablet arm is provided. In one embodiment the tablet arm includes an upper portion configured to rotate a mounted electronic device relative to a central axis of the upper portion and a lower portion coupled to the upper portion and extending downwards, away from the upper portion along a vertical axis perpendicular to the central axis, the upper portion and lower portion forming a hollow structure configured to house cables of an electronic device.

17 Claims, 9 Drawing Sheets

(56) References Cited

OTHER PUBLICATIONS

CN application 201911128071.9 filed Nov. 18, 2019—First Office Action dated Mar. 22, 2021; 7 pages.
TW201328356 English translation of Abstract; Espacenet search results May 27, 2021.
"Mobile C-arms," Siemens Healthcare Website, Available Online at https://usa.healthcare.siemens.com/surgical-c-arms-and-navigation/mobile-c-arms/cios-alpha, Available Online as Early as Oct. 10, 2014, 4 pages.
"Ziehm Imaging," Ziehm Website, Available Online at https://www.ziehm.com/en/home.html, Available Online as Early as Jun. 1, 2018, 4 pages.

* cited by examiner

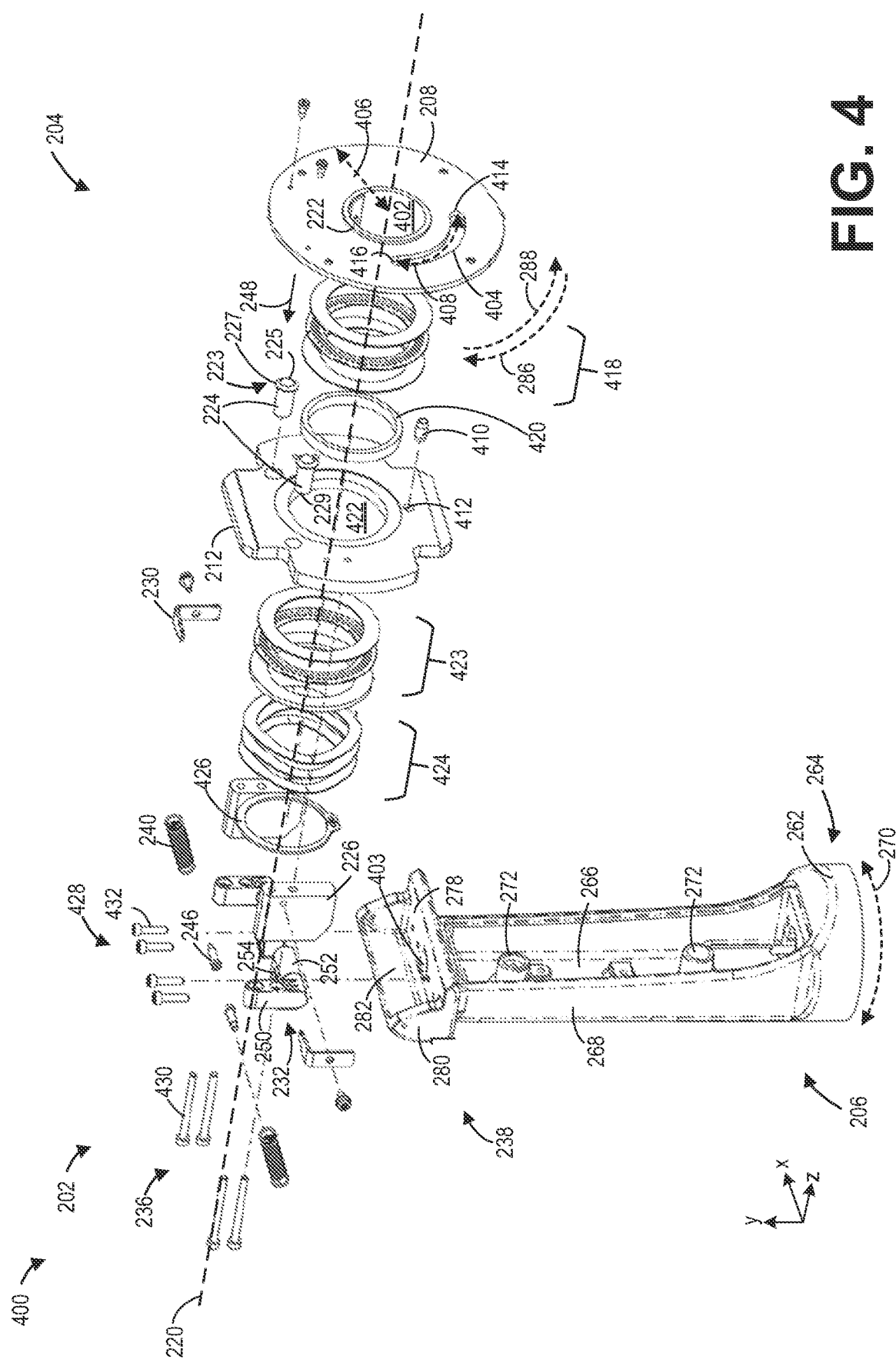

METHODS AND SYSTEMS FOR A PIVOTABLE TABLET MOUNT

FIELD

Embodiments of the subject matter disclosed herein relate to devices for displaying x-ray images and controlling x-ray imaging systems.

BACKGROUND

Mobile C-arm x-ray imaging systems have been developed to allow x-ray examination of a patient from different positions without repositioning the patient. The C-arm x-ray imaging systems are preferably used in the medical and surgical arts due to their small size, mobility and ability to provide high-resolution x-ray images in real time. During an operation, the C-arm x-ray imaging systems may be used to monitor progress during the operation and immediately perform any corrective actions that may be required during the procedure. The x-ray images are displayed on a device with a monitor, such as a tablet, that is coupled to the C-arm x-ray imaging systems by an arm.

The tablet displays x-ray images in high-definition as the images are generated and electronically stores image data. The tablet may be configured to interface with an x-ray imaging system to allow a user to operate the system through touch-sensitive digital controls on the tablet. Thus the tablet serves both as a display device and a system controller.

BRIEF DESCRIPTION

In one embodiment, a tablet arm includes an upper portion configured to rotate a mounted electronic device relative to a central axis of the upper portion and a lower portion coupled to the upper portion and extending downwards, away from the upper portion along a vertical axis perpendicular to the central axis, the upper portion and lower portion forming a hollow structure configured to house cables of an electronic device.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 4 shows an example of an arm for coupling a tablet device to a C-arm x-ray imaging system in an exploded view.

DETAILED DESCRIPTION

Figure 1:
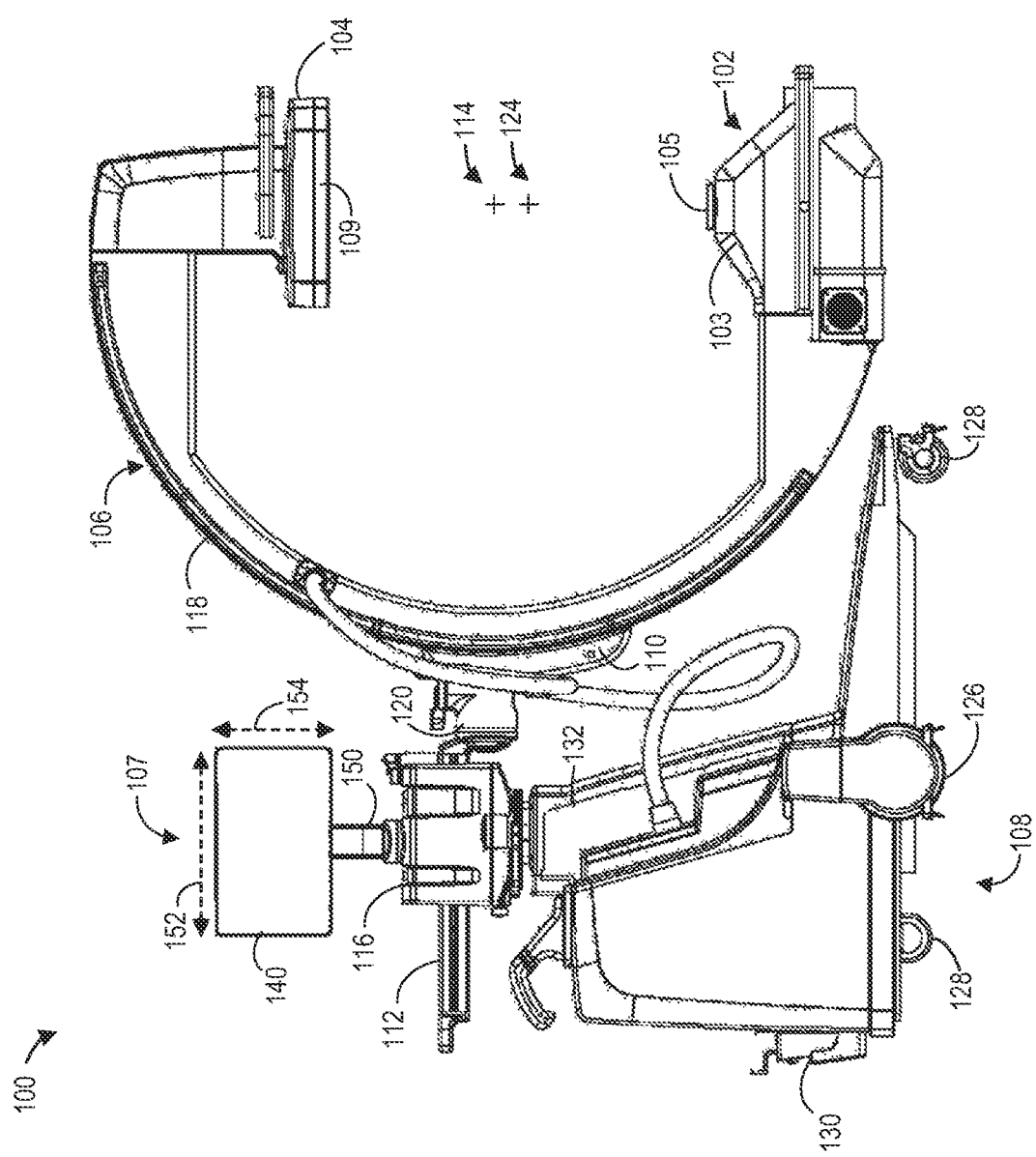
FIG. 1 shows an example C-arm x-ray imaging system according to an embodiment.
Figure 2:
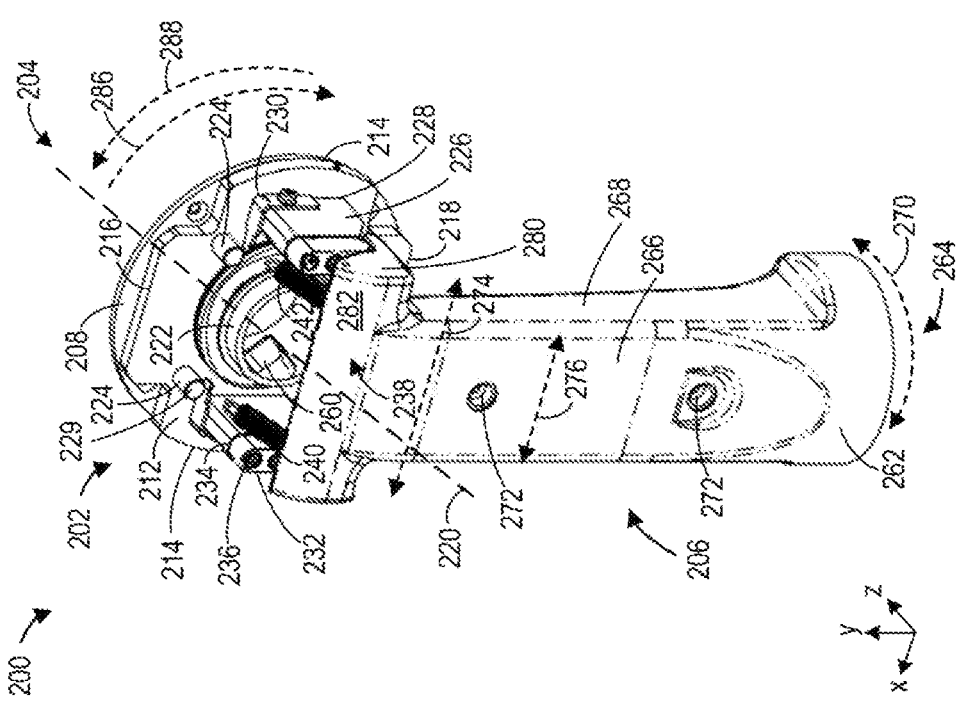
FIG. 2 shows an example of a tablet arm, from a rear perspective view, used to couple a tablet to a C-arm x-ray imaging system according to an embodiment.
Figure 7:
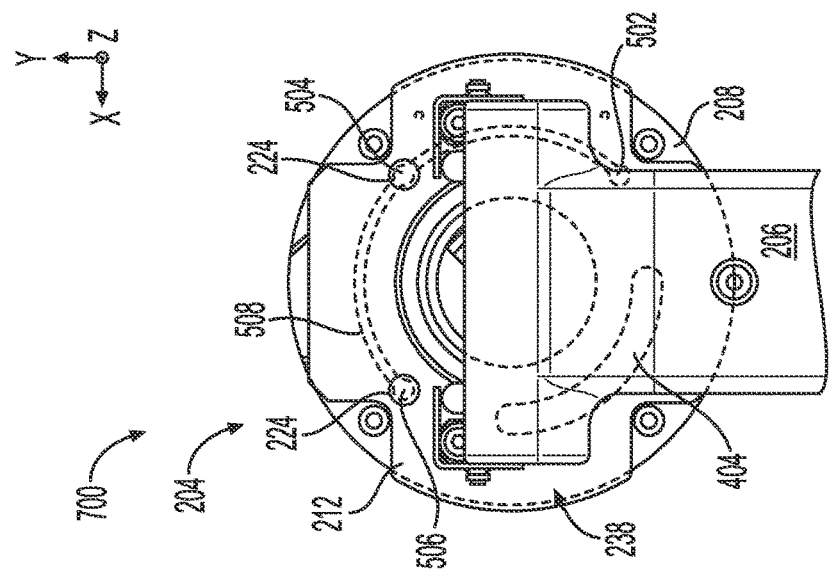
FIG. 7 shows the example of an arm for coupling a tablet device to a C-arm x-ray imaging system in a third position.
Figure 6:
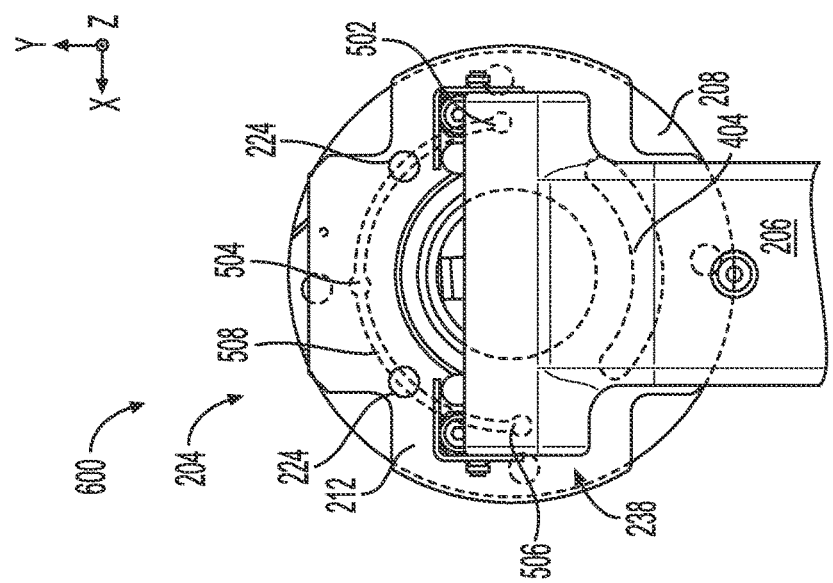
FIG. 6 shows the example of an arm for coupling a tablet device to a C-arm x-ray imaging system in a second position.
Figure 5:
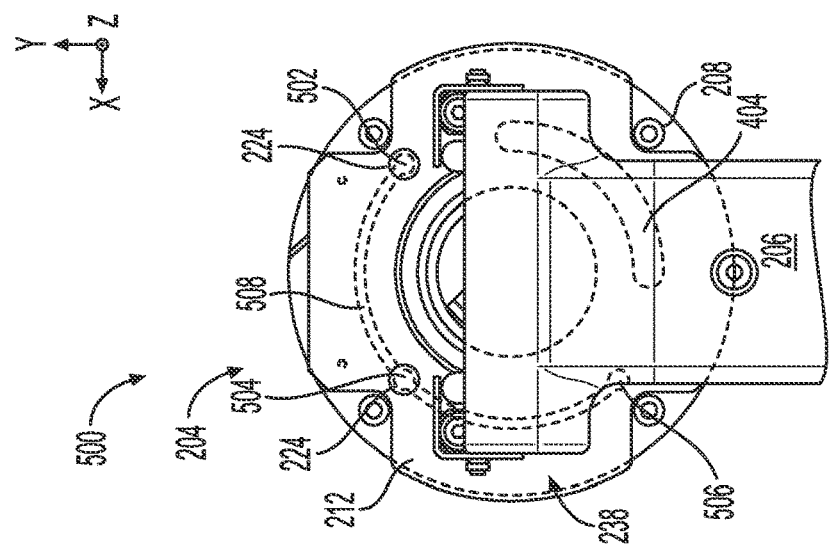
FIG. 5 shows an example of an arm for coupling a tablet device to a C-arm x-ray imaging system in a first position.
Figure 8:
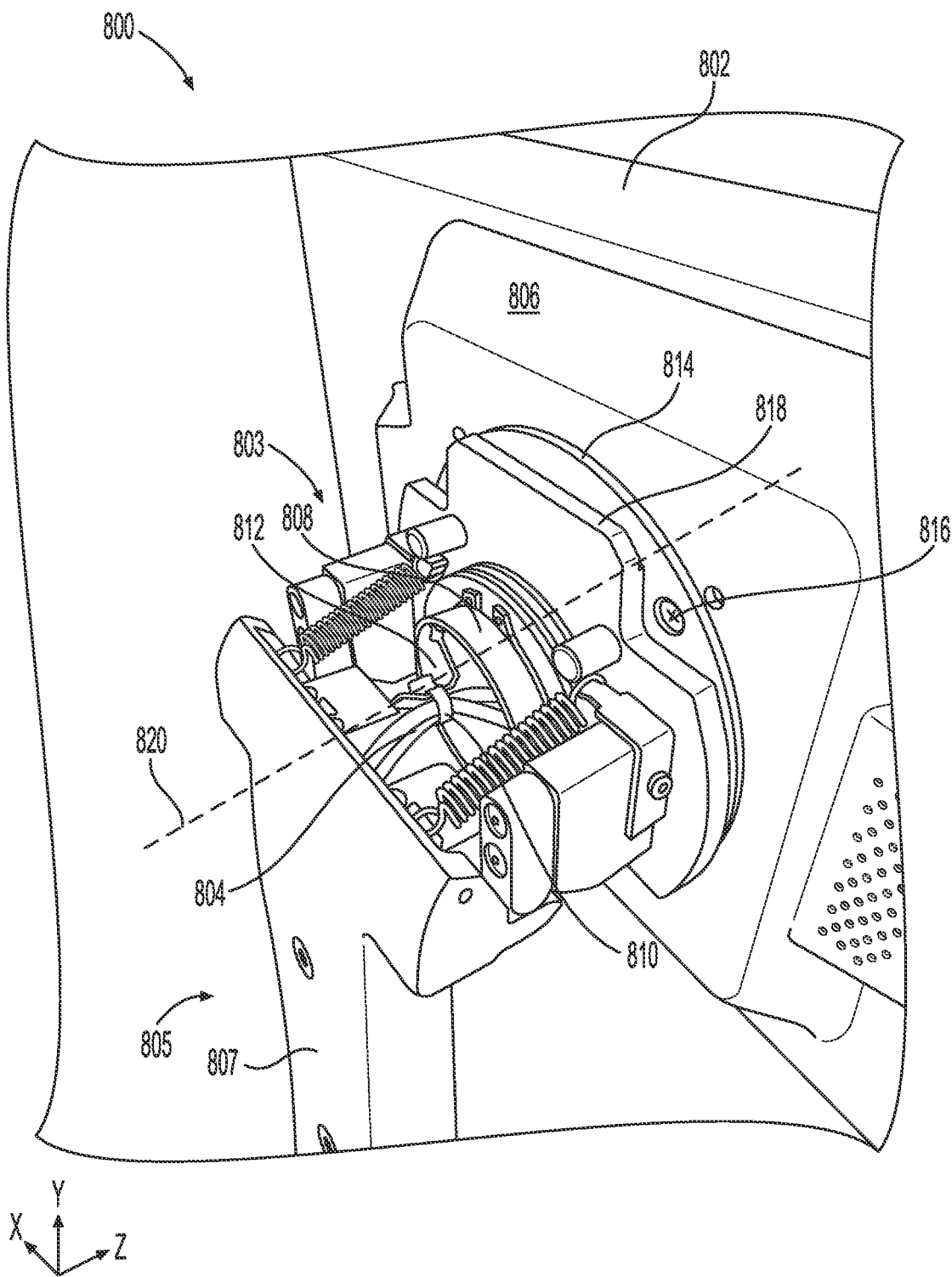
FIG. 8 shows an example of an arm coupled to a tablet device in a first position.
Figure 9:
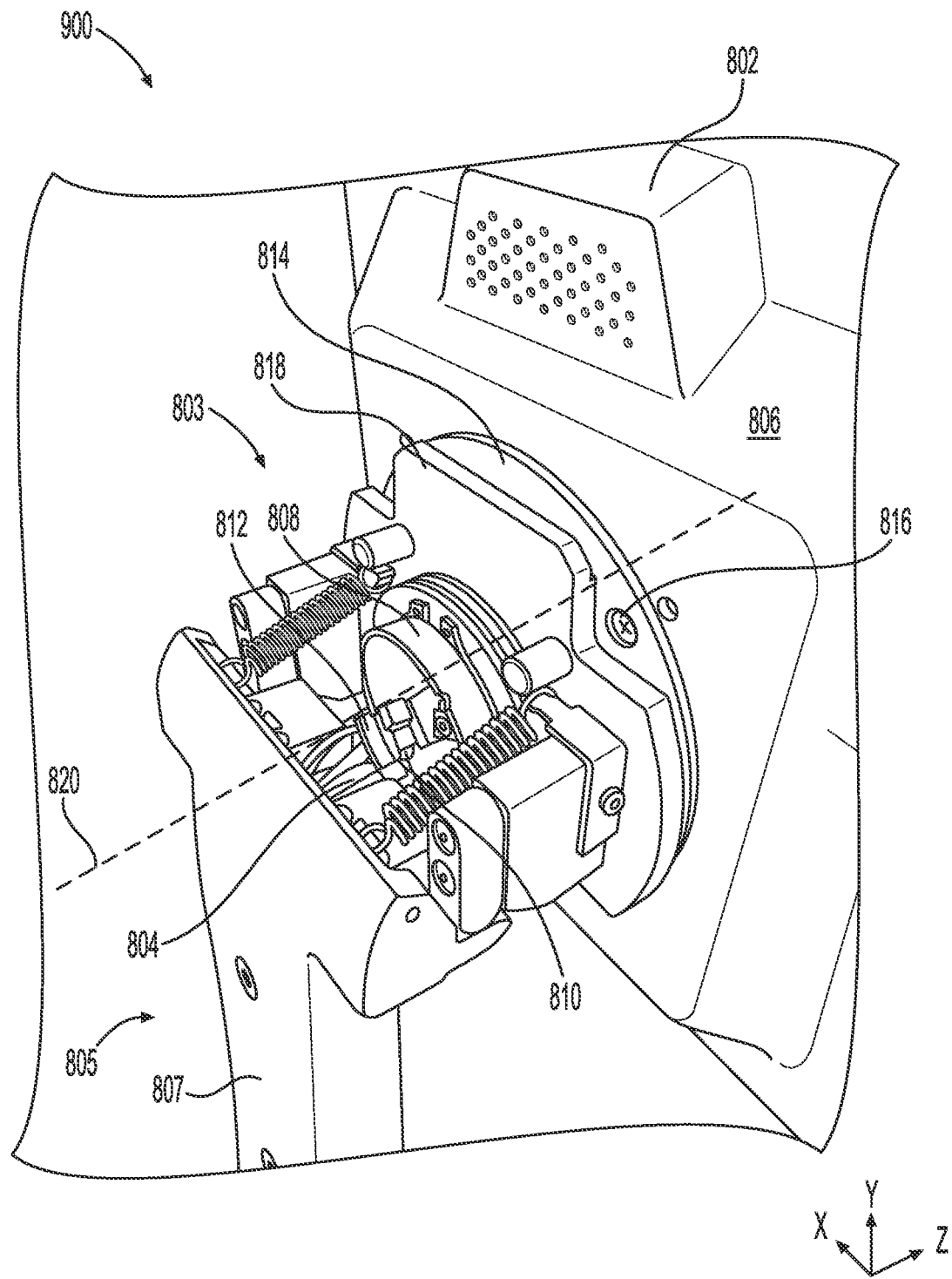
FIG. 9 shows the example of the arm coupled to the tablet device in a second position.
Figure 13:
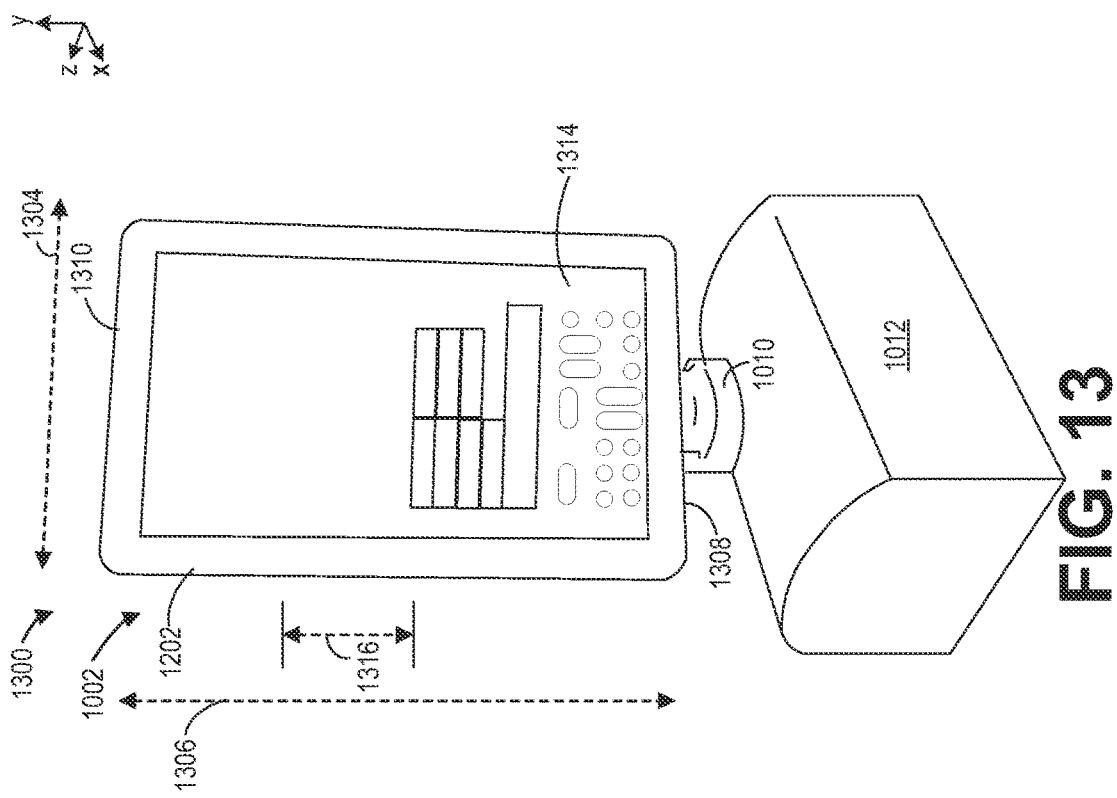
FIG. 13 shows the example of the arm coupled to the tablet device with the tablet device in the portrait orientation, from the front perspective view of the tablet device.

The following description relates to various embodiments of a tablet arm for an x-ray imaging system. As depicted in FIG. 1, a C-arm x-ray imaging system includes a display tablet device coupled to the x-ray imaging system via an arm. The arm provides a secure mount for the tablet device so that x-ray images may be readily viewed by a user. The tablet device may also display an interactive control panel that allows the user to operate the x-ray imaging system. To adjust a viewing perspective of the tablet device display, the arm includes a joint that allows the tablet device to be tilted or rotated. An example of an arm that may be used to couple the tablet device to the x-ray imaging system is shown in FIG. 2 from a rear perspective view and from a side cross-sectional view in FIG. 3. The arm may include a plurality of components that enable tilting of the tablet device and adjustment of the tablet device between a vertical, portrait orientation and a horizontal, landscape orientation while accommodating cables connected to a rear side of the tablet device. The plurality of components are shown in an exploded view in FIG. 4 and include a mounting plate that is attached to a rear side of the tablet device. The mounting plate may be configured to rotate through an angle to alternate the position of the tablet device between the portrait and landscape orientations without removing the tablet device or detaching the cables. Pivoting of the mounting plate between three different positions within the angle of rotation of is shown in FIGS. 5-7. The pivoting of the mounting plate and tablet device, between the landscape and the portrait orientations, are shown in FIGS. 8-9 without a cover over an upper portion of the arm to illustrate a positioning of the cables between the two orientations when the cables are coupled to the rear side of the tablet along an axis of rotation of the tablet device. The tablet device is depicted from a rear view in FIGS. 10 and 11 with the cover in place over the upper portion of the arm. Dimensions of the arm may be adapted to allow clearance for pivoting of the tablet device between the landscape and portrait orientations without the tablet contacting a lower portion of the arm or other components of the x-ray imaging system. A display of the tablet device, including a control panel for the x-ray imaging system as well as an x-ray image, may be oriented differently between the portrait and landscape orientations, as shown a front view of the tablet device in FIGS. 12 and 13. The arm and the tablet device may also be swiveled at a base of the arm, as depicted in FIGS. 12-13 relative to FIGS. 10-11. In addition to rotating and swiveling, a plane of the tablet device may be tilted with respect to the arm, as shown in a side of view of the tablet device and the arm in FIGS. 14-15.

X-ray imaging may be used to obtain images of internal parts of a patient. Such imaging is used in the healthcare sector to diagnose and monitor a variety of conditions including, for example, injuries to the patient's skeleton, such as breaks and fractures, vascular health, or to identify cancerous growths. By using a mobile C-arm x-ray imaging system, a more efficient system than conventional stationary x-ray systems for obtaining internal images is provided. In particular, the C-arm x-ray imaging system is useful in an operating room where re-positioning of operating staff and equipment occurs with high frequency. The C-arm x-ray imaging system may be readily maneuvered around the patient, thereby allowing the patient to remain stationary and comfortable.

FIG. 1 shows an example mobile C-arm x-ray imaging system 100. The C-arm x-ray imaging system 100 includes an x-ray source 102 and an x-ray detector 104 mounted on a C-arm gantry 106. The x-ray source 102 is disposed within a housing 103 and includes a collimator 105. The collimator 105 may comprise any suitable x-ray attenuating material such as tungsten, lead, gold, copper, etc., and may be used to focus an x-ray beam emitted at the x-ray source 102 while minimizing exposure of a patient to x-rays.

The C-arm gantry 106 is coupled to a mobile base 108 of the mobile x-ray imaging system 100 via a C-arm carrier 110 and a movable arm 112. The C-arm carrier 110 and the movable arm 112 may be controlled by a system controller 107 to adjust a position of an imaging isocenter 114, also referred to herein simply as isocenter 114, relative to the mobile base 108, to adjust a position of the C-arm gantry 106 relative to the mobile base 108, and/or to adjust a position of the x-ray source 102 and the x-ray detector 104 relative to the isocenter 114. To be specific, the isocenter 114 of the C-arm gantry 106 comprises the intersection of the optical axis (defined by a focus of the x-ray source 102 and the center of the x-ray detector 104 or the normal to the x-ray detector 104 that goes through the focus) and the C-arm rotation axis along the C-arm carrier 110.

The x-ray detector 104 includes a square or rectangular flat panel detector 109. In other examples, the flat panel detector 109 may have various geometries, such as circular, hexagonal, oval, etc. Dimensions of the flat panel detector 109, such as length, width, radius, or circumference, may define an active or receptive area of the flat panel detector 109. The flat panel detector 109 may be a complementary metal-oxide semiconductor (CMOS) or a crystalline silicon (c-Si) based detector, adapted to facilitate nearly continuous zooming.

The C-arm carrier 110 is coupled to the C-arm gantry 106 and configured to rotate the C-arm gantry 106 along a gantry track 118 in the depicted x-y plane. To that end, the C-arm carrier 110 may include one or more motors (not shown) for sliding the C-arm gantry 106 along the gantry track 118. The C-arm gantry 106 may be rotated in the x-y plane about a rotation axis or the isocenter 114 relative to the C-arm carrier 110, such that the x-ray source 102 and the x-ray detector 104 are rotated relative to the isocenter 114 in the x-y plane.

In addition, the C-arm carrier 110 further comprises a support base 120 mechanically coupled to the C-arm carrier 110 as depicted. The support base 120 is in turn mechanically coupled to the movable arm 112. The support base 120 may be adapted to rotate in the y-z plane, thereby also rotating the C-arm gantry 106 in the y-z plane. The movable arm 112 may be configured to slide along the x-axis, thereby extending or retracting the C-arm-gantry along the x-axis. Movement of the movable arm 112 may be actuated by a bearing assembly 116. In this way a positioning of the C-arm gantry 106 is adjustable in 3-dimensional space, allowing an orientation of the C-arm gantry 106 to accommodate a patient according to the patient's position, e.g., seated versus prone and also accommodate a location of a region of the patient to be imaged.

A combination of adjustments to a position of the movable arm 112 and to a position of the support base 120 may vary an orientation of an imaging center 124 of the C-arm gantry 106 relative to the patient. For example, controlling the movable arm 112 enables a translation of the imaging center 124 in the depicted x-y plane. Furthermore, rotation of the C-arm gantry 106 in the y-z plane via the support base 120, as well as rotation of the C-arm gantry 106 relative to the C-arm carrier 110, adjusts the relative position of the x-ray source 102 and the x-ray detector 104 relative to the imaging center 124 in three-dimensional space.

As described above, the C-arm gantry 106 is coupled to the mobile base 108 via the C-arm carrier 110, support base 120, and the movable arm 112. The mobile base 108 includes a plurality of wheels including driven wheels 126 and free wheels 128. The driven wheels 126 may be driven by one or more motors 130 for moving the mobile base 108 and thus the entire mobile x-ray imaging system 100. In addition to moving the mobile x-ray imaging system 100 along the x-axis (i.e., to the left and right), the motor 130 may drive the driven wheels 126 in the z direction, thus enabling the mobile x-ray imaging system 100 to be re-positioned in any orientation in the x-z plane. As an example, two motors 130 for each of the driven wheels 126 may be provided, wherein one motor 130 comprises a traction motor and a second motor 130 comprises a direction motor. In other examples, dual wheels (with differential traction motors), omnidirectional wheels, or other types of motorized wheels may be used. The free wheels 128 may not be driven by a motor. Further, as depicted, the driven wheels 126 may be positioned in the front of the mobile base 108 (i.e., on the side of the mobile base 108 closer to the C-arm gantry 106) and thus may be advantageously positioned closer to the center of gravity of the mobile x-ray imaging system 100. In some examples the free wheels 128 may be positioned at the front side of the mobile base 108 on a structure extending towards the C-arm gantry 106. In some examples, all wheels of the mobile x-ray imaging system 100 may be driven wheels 126.

In some examples, the mobile x-ray imaging system 100 may include a high voltage generator (not shown) housed within a housing 132 of the mobile base 108. Providing the high voltage generator within the mobile base 108 increases the weight of the mobile base 108, thus stabilizing the mobile x-ray imaging system 100. Furthermore, providing the high voltage generator within the mobile base 108 eliminates the need to house the high voltage generator remotely from the mobile x-ray imaging system 100, thereby eliminating long high-voltage cables typically connected to the x-ray source 102 via a tether for providing the x-ray source 102 with high voltages. In addition, some examples may include an on-board generator, a heat exchanger, and a battery at the mobile base 108 to enable fully autonomous operation of the mobile x-ray imaging system 100.

The mobile x-ray imaging system 100 may be operated by the system controller 107. In one example, the system controller 107 may be a tablet device 140 with an integrated computing environment and display monitor. The system controller 107 may include one or more processing units in a variety of customizable enterprise configurations, including in a networked or combination configurations. The system controller 107 may include one or more computer readable media, wherein each medium may be configure to include data or computer executable instructions such as data structures, objects, programs, routines, or other program modules that may be accessed by the one or more processors.

The computer executable instructions may cause the one or more processors of the enterprise to perform a particular function or group of functions are may be examples of program code means for implementing steps for methods of processing. Furthermore, a particular sequence of the executable instructions provides an example of corresponding acts that may be used to implement such steps.

Examples of computer readable media include random-access memory ("RAM"), read-only memory ("ROM"), programmable read-only memory ("PROM"), erasable programmable read-only memory ("EPROM"), any solid state storage device (e.g., flash memory, smart media, etc.) or any other device or component capable of providing data or executable instructions that may be accessed by the one or more processors. The one or more processors may include a central processing unit (CPU) and one or more processors configured to perform a particular task. The one or more processors may execute the instructions provided on computer readable media, such as on the memory(ies), or from a communication connection.

A data manipulating system may be included in the CPU that may be used to enable data and/or instructions to be exchanged with the CPU through one or more peripheral I/O devices, such as a mouse or a printer, etc. Information may be exchanged via the data manipulating system across one or more network interfaces including a connection that allows data to be exchanged between processing units, a network adapter for connection to a local area network ("LAN"), or a wireless link for connection to a wide area network ("WAN"), such as the Internet.

The tablet device 140 may thus be used directly connected, via cables, to the mobile x-ray imaging system 100 to control operation of the mobile imaging x-ray system. The tablet device 140, in addition to storing and executing instructions stored in the memory(ies) of the system controller 107, may also display images obtained by the mobile x-ray imaging system 100. The system controller may include an imaging control subsystem that is configured to display an image on the monitor of the tablet device 140. For example, x-ray images obtain in real-time may be immediately displayed on the tablet device screen during operation of the mobile x-ray imaging system 100. The images may be stored in the memory(ies) of the system controller 107 and may be sent over the network interfaces for further storage, processing etc.

The display screen of the tablet device 140 may be implemented with touch-screen technology to provide a touch-screen user interface. An operator may manipulate the displayed x-ray image by tapping, swiping, pinching, dragging, or otherwise moving the operator's fingers in contact with the tablet device screen to move an image, hone in on a region of the image or zoom in/out. Furthermore, a control panel may be displayed on the tablet device monitor to adapt control of the mobile x-ray imaging system 100 to the touch-screen user interface. The control panel may include an array of buttons, simulating a physical control panel that may be included in a conventional x-ray imaging system. The array of buttons may allow the operator to activate/deactivate the x-ray source 102, adjust a position of the C-arm gantry 106, save images, send images over the network interfaces, etc.

When the system controller 107 is connected to a WAN by a wireless link, the tablet device 140 may be detached from the cables coupling the tablet device 140 the mobile x-ray imaging system 100 as well as a power source, and used to manipulate x-ray images at an alternate location, e.g., in another room or building. In some examples, the mobile x-ray imaging system 100 may be adapted with wireless capabilities and the detached tablet device 140 may be used to operate the mobile x-ray imaging system 100 by the WAN. When connected to the mobile-x-ray imaging system 100 and to the power source, the tablet device 140 may be mounted on a tablet arm 150. In a conventional tablet arm 150, the tablet device may be mounted in a fixed position where a width 152 of the tablet device 140 is greater than a height 154 of the tablet device 140, e.g., a landscape orientation, as shown in FIG. 1.

In the landscape orientation, the width 152 of the tablet device 140 may obstruct the operator's view of the patient positioned within the C-arm gantry 106 when the operator is operating the mobile x-ray imaging system via the control panel on the tablet device screen. The x-ray image and control panel displayed on the tablet device screen may also be in a fixed configuration with the image and control panel arranged adjacent to one another along the x-axis. The operator may resort to swiveling the tablet device 140, if the tablet arm 150 is configured to rotate at a base of the tablet arm 150, to widen the operator's field view to include the patient or a staff member assisting the patient. However, swiveling the tablet device 140 may obscure the operator's view of the tablet device screen.

Use of the tablet device 140 may be made more flexible and accommodating towards visibility for the mobile x-ray imaging system operator by configuring the tablet arm to allow at least 90 degree rotation of the tablet device 140. Rotating the tablet device 140 may adjust a position of the tablet device 140 so that the width 152 becomes the height of the tablet device 140 while the height 154 becomes the width, the new width 154 smaller than the new height 152 of the tablet device 140. The tablet device is thus adjusted to a portrait orientation, the portrait orientation narrower in width and taller in height than the landscape orientation.

Pivoting of the tablet device 140 between the landscape and portrait orientations may be performed without detaching the cables from the tablet device 140 or imposing excessive strain at connection points between the cables and the tablet device 140 by adapting the tablet device 140 to couple to the cables at a rear side of the tablet device 140, the rear side opposite of the tablet device screen. Conventional tablet devices for mobile x-ray imaging systems may have cable ports disposed along an edge of the tablet device 140. Edge-wise coupling to cables may result in pulling and sweeping of cables when rotating the tablet device 140 between the landscape and portrait orientations. However, when the cables are instead connected at the rear side of the tablet device 140 and extend from the rear side away from the tablet device 140, along an axis of rotation of the tablet device 140, the cables may experience minimal torque during pivoting of the tablet device 140. Furthermore, the cables may be enclosed within the tablet arm 150, thereby containing the cables within a rigid supporting frame and shielding the cables from contact with external objects.

The tablet arm 150 may include two portions; a rotatable and tiltable head that couples directly to the rear side of the tablet device 140 and a stem that extends along the y-axis between the tablet device and an outer housing of the bearing assembly 116. The stem may intersect with the head at a first, top end of the stem and attach to the outer housing of the bearing assembly 116 at a second, bottom end. As such, the tablet arm 150 may enable the tablet device 140 to be adjusted between the landscape and portrait orientations while remaining connected to the tablet arm 150 and without detaching the cables from the rear side of the tablet device 140.

Figure 3:
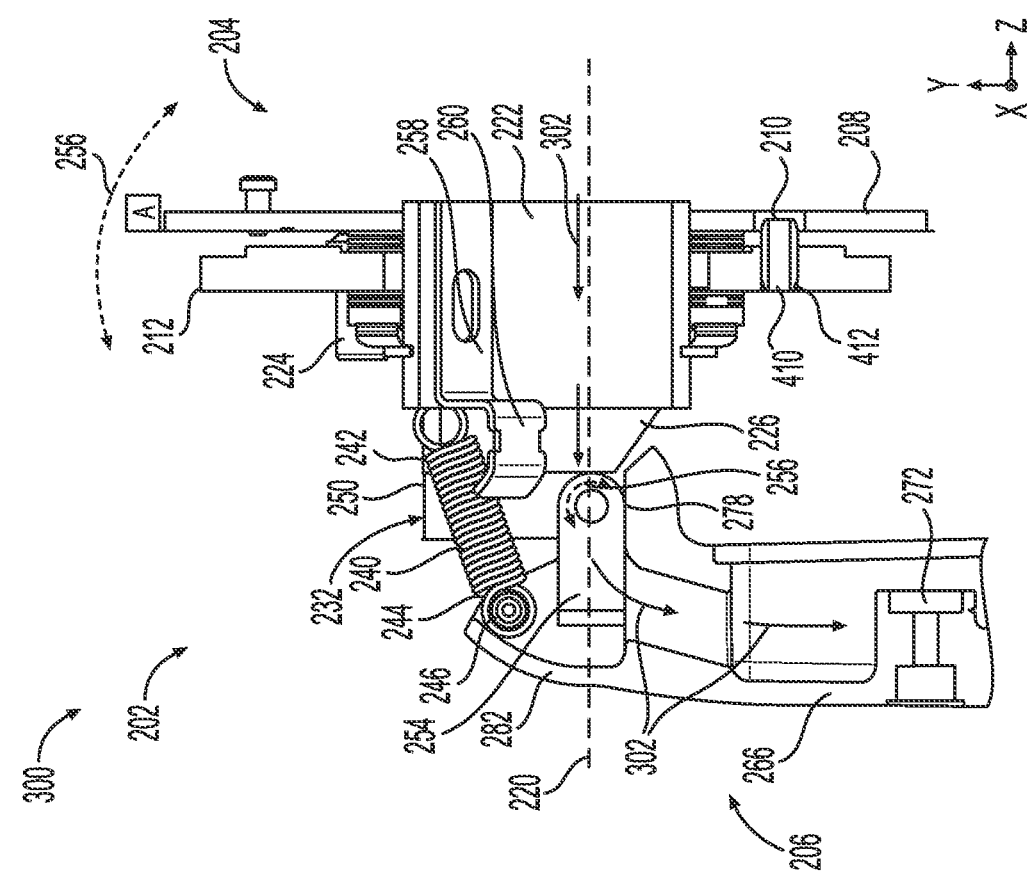
FIG. 3 shows an example of an arm, from a cross-sectional view, used to couple a tablet device to a C-arm x-ray imaging system.

An example of a tablet arm 202 that may be used to alternate a position of a tablet device between a landscape orientation and a portrait orientation is shown in FIG. 2 from a rear perspective view 200 and from a side cross-sectional view 300 in FIG. 3. Similar components are similarly numbered in FIGS. 2, 3, and 4 for brevity. The tablet arm 202 may be used similarly as the tablet arm 150 of FIG. 1, positioned between a tablet device and an outer housing of a bearing assembly. The tablet arm 202 has a rotatable and tiltable head 204 coupled to a stem 206 that is an elongate shell extending vertically along the y-axis. The head 204 forms a joint of the tablet arm 202 that allows tilting and pivoting of the tablet device when the tablet device is mounted to the head 204.

The head 204 may include a number of components that are in shown in greater detail in an exploded view 400 of the tablet arm 202 in FIG. 4. The head 204 includes a circular mounting plate 208 that may be in face-sharing contact with a rear side of the tablet device, e.g., a front-facing surface of the mounting plate 208 is in direct contact with the rear side of the tablet device. The mounting plate 208 has a central aperture 402, shown in FIG. 4, arranged at a geometric center of the mounting plate 208 and extending entirely through a thickness of the mounting plate 208, the thickness defined along the z-axis. A curved slot 404, forming an elongate through-hole through the thickness of the mounting plate as shown in FIG. 4, may be disposed in the mounting plate 208 at a mid-point of a radius 406 of the mounting plate 208 between an inner edge of the mounting plate 208 defining the central aperture 402 and an outer edge of the mounting plate 208. The curved slot 404 may have a length 408 that is equal to a quarter of a circumference of the mounting plate 208 at the mid-point of the radius 406 where the curved slot 404 is disposed. The curved slot 404 may have a width, the width perpendicular to the central axis 220 and perpendicular to the length 408 of the curved slot 404, that is configured to accept a stop pin 410 of a tilt plate 212, described further below.

The mounting plate 208 may have a plurality of circular pockets, as shown in FIGS. 5-7, extending through at least a portion of the thickness of the mounting plate 208. The plurality of pockets may be rounded recesses in a rear-facing surface of the mounting plate 208 with central apertures that may extend entirely through the thickness of the mounting plate 208. The plurality of pockets may be adapted to receive and engage with ball spring plungers 224 of the tilt plate 212.

The ball spring plungers 224 may be cylindrical tubes extending through a thickness of the tilt plate 212, the thickness defined along a central axis 220 of the head 204. As shown in FIG. 4, first ends 223 of the ball spring plungers 224 may protrude from a front-facing surface of the tilt plate 212 and may include balls 225 held in place within the ball spring plungers 224 at the first ends 223 by pressure from inner springs housed within the ball spring plungers 224. The balls 225 may slide translationally along the z-axis into the ball spring plungers 224 when pressure is applied to the balls 225 in a direction indicated by arrow 248. The first ends 223 of the ball spring plungers 224 may also include clips 227 that secure a positioning of the ball spring plungers 224 through the thickness of the tilt plate 212, defining an amount that the ball spring plungers 224 protrude from the front-facing surface of the tilt plate 212. Second ends 229 of the ball spring plungers 224 may protrude along the central axis 220 from a rear-facing surface of the tilt plate 212.

The stop pin 410, as shown in FIG. 4, may also protrude along the z-axis from the front-facing surface of the tilt plate 212. The stop pin 410 may be inserted into a hole 412 in the front-facing surface of the tilt plate 212, the hole 412 extending into at least a portion of the thickness of the tilt plate 212. A diameter of the stop pin 410 may be similar to or slightly larger than a diameter of the hole 412 so that the stop pin 410 is press fit into the hole 412 and held securely by the hole 412.

The stop pin 410 may be configured to protrude from the front-facing surface of the tilt plate 212 by a greater distance along the z-axis than the ball spring plungers 224. When components of the head 204 of the tablet arm 202 are assembled, the stop pin 410 is inserted into the curved slot 404 of the mounting plate 208. The diameter of the stop pin 410 may be similar to or slightly smaller than the width of the curved slot 404 so that the stop pin 410 may slide freely within the curved slot 404. In this way, the mounting plate 208 may be rotated through a 90 degree angle, as indicated by arrows 286 and 288 in FIG. 2, relative to the tilt plate 212 and the stem 206 of the tablet arm 202. Rotation of the mounting plate 208 may be halted by contact between an end of the curved slot 404 and the stop pin 410.

For example, when the mounting plate 208 is rotated according to arrow 286 in FIG. 4, rotation of the mounting plate 208 may stop when a first end 414 of the curved slot 404 contacts the stop pin 410, the stop pin 410 inserted through the curved slot 404. When the mounting plate 208 is rotated in an opposite direction, indicated by arrow 288, the rotation of the mounting plate is terminated by contact between the stop pin 410 and a second end 416 of the curved slot 404. Furthermore, a position of the mounting plate 208 when the stop pin 410 is in contact with either the first end 414 or the second end 416 of the curved slot 404 may coincide with alignment of the ball spring plungers 224 with the plurality of pockets in the rear-facing surface of the mounting plate 208.

As an example, when the mounting plate 208 is rotated into a first position as indicated by arrow 286 until the stop pin 410 contacts the first end 414 of the curved slot 404, the first ends 223 of the ball spring plungers 224 may align with two of the plurality of pockets in the rear-facing surface of the mounting plate 208, as shown in FIG. 2. When the mounting plate 208 is oppositely rotated as indicated by arrow 288 until the stop pin 410 contacts the second end 416 of the curved slot 404 in a second position of the mounting plate 208, the ball spring plungers 224 may again align with two of the plurality of pockets. If amount of rotation of the mounting plate 208 is 90 degrees, one of the two pockets is a same pocket as the two pockets engaging with the ball spring plungers 224 in the first position and the other pocket is a different pocket. When the ball spring plungers 224 are engaged with the plurality of pockets, the balls 225 at the first ends 223 of the ball spring plungers 224 are inserted into the plurality of pockets and the mounting plate 208 may be locked in place. However, by exerting a pressure on the mounting plate 208, along the directions indicated by arrow 286 or 288, that overcomes a spring force exerted on the balls 225 by the springs housed within the ball spring plungers 224, the mounting plate 208 may be unlocked and rotated.

When the ball spring plungers 224 are not aligned with the plurality of pockets, the balls 225 at the first ends 223 of the ball spring plungers 224 may be in contact with the rear-facing surface of the mounting plate 208 and depressed into the ball spring plungers 224. Thus, an extent of rotation of the mounting plate 208 is controlled by interaction of the stop pin 410 with the curved slot 404 enabling locking of the mounting plate 208 between two positions, the two positions corresponding to contact between the stop pin 410 and ends of the curved slot 404 and alignment of the ball spring plungers 224 with the plurality of pockets in the mounting plate 208.

Rotation of the mounting plate 208 relative to the tilt plate 212 and the stem 206 of the tablet arm may be further illustrated in FIGS. 5-7. A first position 500 of the mounting plate 208 is shown in FIG. 5 which may correspond to 0 degrees of rotation, a second position 600 in FIG. 6 which may correspond to 45 degrees of rotation, and a third position 700 in FIG. 7 which may correspond to 90 degrees of rotation, the rotation in a clockwise direction. A first pocket 502, a second pocket 504, and a third pocket 506 of the plurality of pockets are disposed in the rear-facing surface of the mounting plate 208. The rear-facing surface of the mounting plate 208 also includes a track 508 that defines a path for the balls 225 at the first ends 223 of the ball spring plungers 224 to travel along the rear-facing surface of the mounting plate 208, the ball spring plungers 224 protruding in a forwards direction from the tilt plate 212. The track 508 may be a shallow recess in the rear-facing surface of the mounting plate 208 with a curvature that maintains the track 508 at a uniform distance from the outer edge and the inner edge of the mounting plate 208. A depth of the track 508 into the rear-facing surface of the mounting plate 208 may be shallower than the plurality of pockets so that the balls of the ball spring plungers 224 are pushed into the ball spring plungers 224 when the balls are not aligned with the plurality of pockets and instead in contact with the track 508. The first pocket 502, second pocket 504, and third pocket 506 may be connected by the track 508 and the first pocket 502 and third pocket 506 may define ends of the track 508.

In the first position 500 illustrated in FIG. 5, the first pocket 502 and the second pocket 504 are engaged with the ball spring plungers 224. The third pocket 506 is not engaged with the ball spring plungers 224. The first pocket 502 is aligned with a ball spring plunger, e.g., of the ball spring plungers 224, on the right and the second pocket 504 is aligned with a ball spring plunger on the left. Rotation of the mounting plate 208 to the second position 600 in FIG. 6 positions the ball spring plungers 224 against the track 508 in between the plurality of pockets and not aligned with any of the plurality of pockets. Further rotation of the mounting plate 208 to the third position 700 shown in FIG. 7 aligns the ball spring plungers 224 with the plurality of pockets. However, in the third position 700, the second pocket 504 engages with the ball spring plunger on the right and the third pocket 506 engages with the ball spring plunger on the left. The first pocket 502 is rotated beyond the ball spring plungers 224 along the clock-wise direction and is not aligned with the ball spring plungers 224.

The increased depth of the plurality of pockets compared to the track 508 allows the balls 225 of the ball spring plungers 224 to protrude out of the first ends 223, due to spring force of the enclosed springs, a greater distance than when the ball spring plungers 224 are in contact with the track 508. The engagement of the ball spring plungers 224 with the plurality of pockets locks mounting plate 208 in place when the mounting plate 208 is in the first position 500 and in the third position 700. Adjustment of the mounting plate 208 between the first position 500 and the third position 700 is achieved by applying a force to the mounting plate in the clockwise direction to adjust the mounting plate 208 from the first position 500 to the third position 700 or a counter-clockwise direction to adjust the mounting plate 208 from the third position 700 to the first position 500. If the force is greater than the spring force exerted on the balls 225 of the ball spring plungers 224 by the springs housed therein, such as 5 lbs of force, the rotational force allows the ball spring plungers 224 to disengage from the plurality of pockets, releasing the mounting plate 208 from the first position 500 or third position 700.

Returning to FIGS. 2-4, the tilt plate 212 is positioned behind the mounting plate 208 and spaced away from the mounting plate 208 by a stack of annular components, the components stacked along the central axis 220, as shown in FIGS. 3 and 4. An outer geometry of the tilt plate 212 may resemble a plus sign with side edges 214 that may be curved to match an outer perimeter of the mounting plate 208, and a top edge 216 and a bottom edge 218 that are both straight and aligned with the x-axis. Each of the mounting plate 208 and the tilt plate 212 (as well as all other components of the head 204), may have a central aperture aligned along and centered about the central axis 220 of the head 204. The mounting plate 208 may be welded to a steel tube 222 at an inner edge of the mounting plate surrounding the central aperture. The steel tube 222 may extend from the central aperture of the mounting plate 208, through the central aperture of the tilt plate 212 in a rearwards direction along the central axis 220. The steel tube 222 may extend along the central axis 220 a distance beyond a stack of components of the head 204 as shown in FIG. 3, circumferentially surrounded by the stack of components.

A set of standoff blocks 226 may be coupled to the rear-facing surface of the tilt plate 212, extending away from the tilt plate 212. A first end 228, proximate to the tilt plate 212, of the set of standoff blocks 226 may support L-shaped spring clips 230, extending up along an outer surface of the set of standoff blocks 226 and across tops of the set of standoff blocks 226 towards the central axis 220. Springs 240 may extend between the spring clips 230, shown detached from the spring clips 230 in FIG. 2, to a top end 238 of the stem 206. The springs 240 may be removably hooked around portions of the spring clips 230 that protrude from the tops of the set of standoff blocks 226 along the x-z plane at first ends 242 of the springs 240. At second ends 244 of the spring 240, the springs 240 may be fixedly coupled to the top end 238 of the stem 206 via posts 246, as shown in FIG. 3.

Friction hinges 232 may be attached to a second end 234 of each of the set of standoff blocks 226 via bolts 236. The friction hinges 232 may each comprise three sections: a first section 250 aligned with the y-axis, a second section 252 aligned with the x-axis, and a third second 254 aligned with the z-axis. The first section 250 is shown in FIGS. 2-4, the second section 252 shown in FIG. 4, and the third section 254 shown in FIGS. 3 and 4. The second section 252 extend from a bottom end of the first section 250 to the third section 254 towards the central axis 220, e.g., the third section 254 is closer to the central axis 220 than the first section 250. The third section 254 extends away from the second section 252 along a rearwards direction.

The friction hinges 232 may be adapted to pivot around an axis of rotation that is aligned with the second section 252, along the x-axis. The pivoting about the second section 252 allows the head 204 of the tablet arm 202 to rotate through an angle, as indicated by arrow 256 shown in FIG. 3. The angle may be 60 degrees, 90 degrees, etc. and may vary based on a size of a tablet device attached to the mounting plate 208. For example, an amount that the friction hinges 232 may be tilted so that the tablet device faces downwards may be bound by contact between a lower edge of the tablet device and the stem 206 of the tablet arm 202. An amount the friction hinges 232 may tilt in an opposite direction so that the tablet device faces upwards may be bound by contact between the head 204 of the tablet arm 202 and the top end 238 of the stem 206. A smaller tablet device may be pivoted through a greater angle than a larger tablet device. The head 204 may be adjusted to any position within the angle of pivoting and the position maintained by friction between surfaces of the first section 250 and the second section 525 that are in contact. As such, the mounted tablet device may be tilted to a desired angle according to a view point or height of the operator and the desired angle maintained until modified by the operator.

Figure 15:
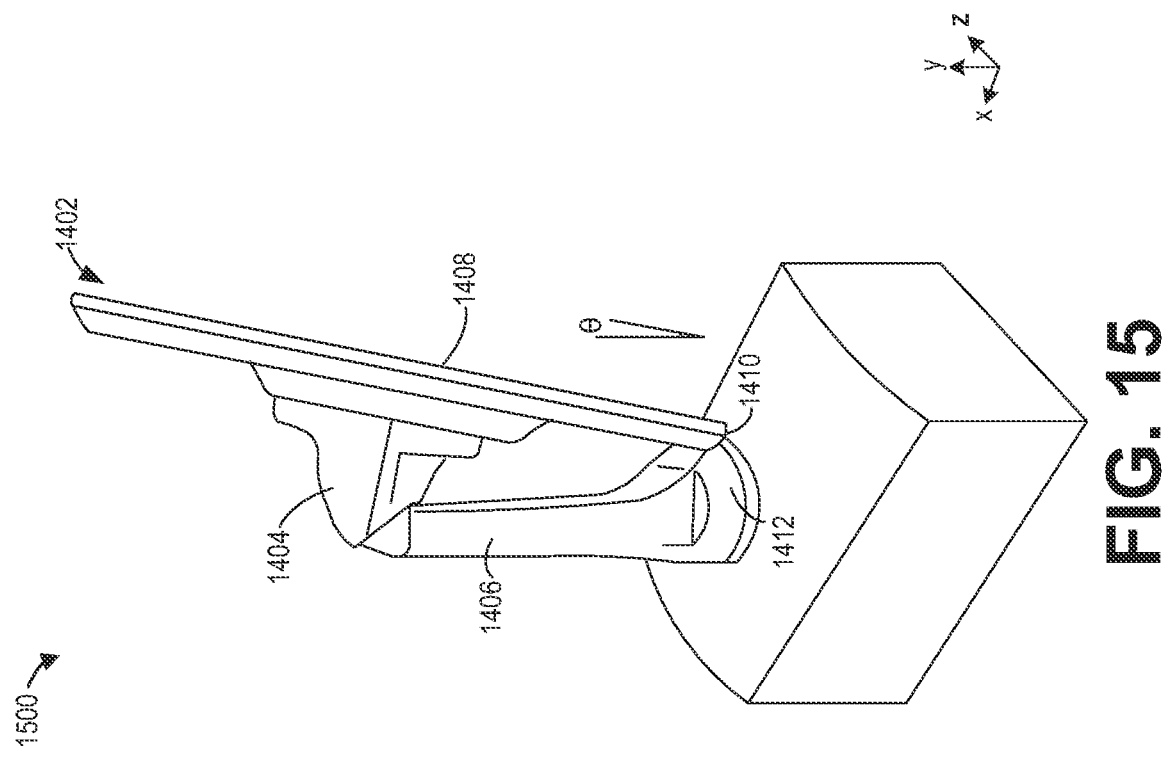
FIG. 15 shows the example of the arm coupled to the tablet device with the tablet device tilted to a second angle, from the side view.
Figure 14:
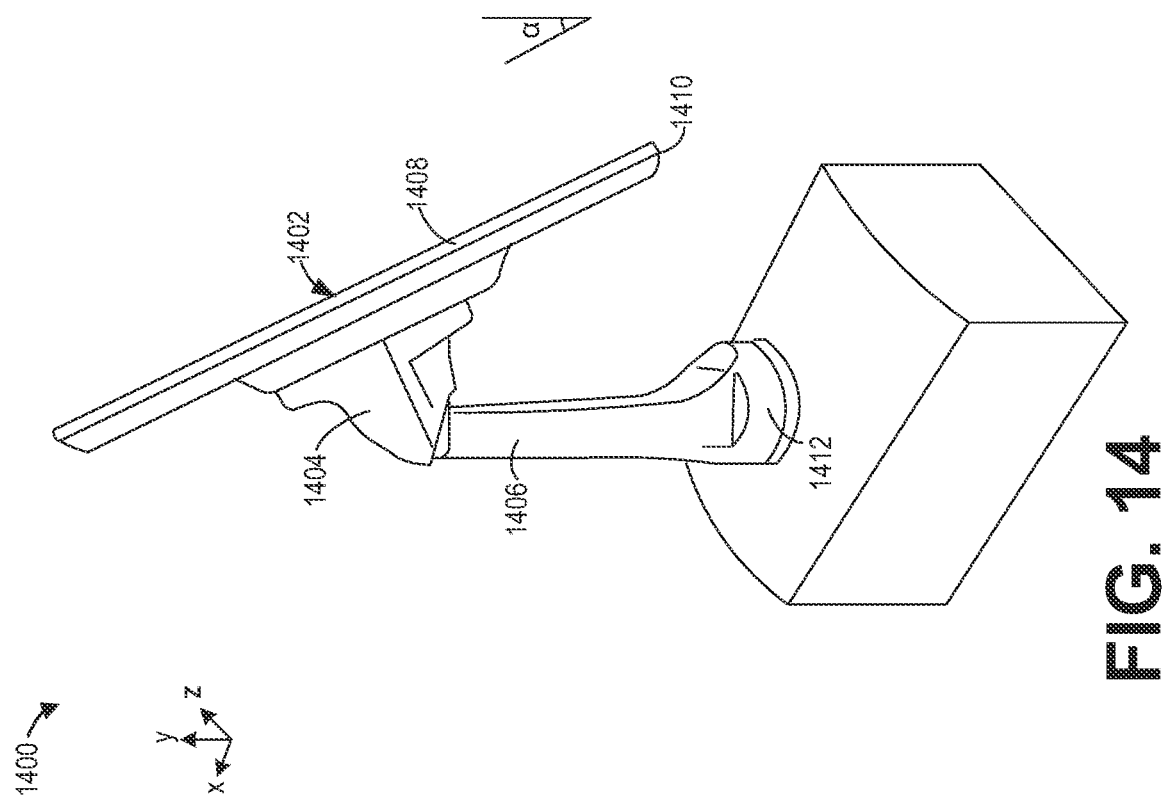
FIG. 14 shows an example of an arm coupled to a tablet device with the tablet device tilted to a first angle, from a side view.

Tilting of a tablet device when mounted on a tablet arm is depicted in FIGS. 14 and 15. In a first position 1400 of FIG. 14, a tablet device 1402, which may be used similarly as the tablet device 140 of FIG. 1, is coupled to a head 1404 of a tablet arm 1406. The head 1404 is tilted in the first position 1400 so that a front-facing surface, e.g. a display screen 1408 of the tablet device 1402, is facing upwards, forming an angle α between a plane of the tablet device and the y-axis. For example, the angle α may be −20 degrees with respect to the y-axis. The head 1404 may also be tilted in an opposite direction, as shown in the second position 1500 in FIG. 15. In the second position 1500, the head 1404 and tablet device 1402 are tilted so that the display screen 1408 is facing downwards. The plane of the tablet device 1402 may form an angle θ with respect to the y-axis of, for example, 10 degrees. The tilting of the head 1404 so that the display screen 1408 of the tablet device 1402 may not be further tilted to turn the display screen to face downwards due to contact between a bottom edge 1410 of the tablet device 1402 and a circular base 1412 of the tablet arm 1406.

Turning back to FIGS. 2-4, the head 204 of the tablet arm 202 may also include a cable zip-tie clip 258, as shown in FIG. 3, arranged in the steel tube 222 and attached to the steel tube 222 by welding or some other method to secure the cable zip-tie clip 258 to the steel tube 222. The cable zip-tie clip 258 may be a strip of metal that extends through the steel tube 222 along the z-axis, with a tail 260 that protrudes out of the steel tube 222 along the rearwards direction. The tail 260 may be hooked, with sections that curve towards and away from the central axis 220.

The stem 206 of the tablet arm 202 may be a rigid hollow shell with a circular base 262, as shown in FIGS. 2 and 4, at a bottom end 264 of the stem 206, the bottom end 264 opposite of the top end 238. Above the circular base 262, the stem 206 may have a planar back wall 266, co-planar with the y-x plane, coupled to side walls 268, the side walls 268 arranged perpendicular to the back wall 266 and on opposite sides of the back wall 266. The side walls 268 may be co-planar with the y-z plane. The back wall 266 and side walls 268 extend from the circular base 262 to the top end 238. The circular base may be coupled to the outer housing of the bearing assembly, e.g., the bearing assembly 116 of FIG. 1, and rotatably attached to the outer housing so that the tablet arm 202 may swivel as indicated by arrow 270. The swiveling of the tablet arm 202 allows the mounted tablet device to also be swiveled relative to the outer housing of the bearing assembly so that the tablet device screen may be viewed from different positions relative to a mobile base of a mobile x-ray imaging system such as the mobile x-ray imaging system 100 of FIG. 1.

The back wall 266 of the stem 206 may include bosses 272 protruding along the z-axis in a frontwards direction. The bosses 272 may be used to couple to matching bosses or pins in a removable front cover for the stem 206 (as shown in FIGS. 12-15) so that the front cover may be attached to the stem 206. The front cover may be a front wall of the stem 206, allowing objects disposed in an interior of the tablet arm 202 to be fully enclosed by walls of the stem 206, e.g., the back wall 266, side walls 268 and the front cover. When cables are threaded through the tablet arm 202, as described below, the front cover may maintain the cables hidden from view.

The top end 238 of the stem 206 may have a width 274 that is wider than a width 276 of the back wall 266 and may or may not be similar to a diameter of the circular base 262. The top end 238 includes a shelf 278 arranged perpendicular to the back wall 266. The shelf 278 may support the head 204 of the tablet arm 202, coupling directly to the second section 252 and the third section 254 of the friction hinges 232, the friction hinges 232 secured to the shelf 278 by a plurality of bolts 428, as shown in FIG. 4. The shelf 278 may include an opening 403 that extends entirely through a thickness of the shelf 278, the thickness defined along the y-axis, and allows air in the interior of the tablet arm 202 above the shelf 278 to exchange with air in the interior of the tablet arm 202 below the shelf 278 via the opening 403. The top end 238 may also have planar side walls 280, co-planar with the y-z plane, arranged on opposite sides of a curved back wall 282 of the top end 238. The curved back wall 282 may have a convex curvature relative to an interior of the tablet arm 202.

As described above, the head 204 of the tablet arm 202 may include a plurality of components stacked along the central axis, behind the mounting plate 208, between the mounting plate 208 and the tilt plate 212, and behind the tilt plate 212. The plurality of stacked components are shown in detail in the exploded view 400 of FIG. 4. In addition to elements previously described with respect to FIGS. 2-4, the head 204 of the tablet arm 202 also includes a first needle bearing stack 418 positioned behind the mounting plate 208 and a bushing 420 that may be inserted within a central aperture 422 of the tilt plate 212. The first needle bearing stack 418 comprises three annular disks. The first needle bearing stack 418 and the bushing 420 may together allow the mounting plate 208 and steel tube 222 to rotate relative to the tilt plate 212. A diameter of the central aperture 422 of the tilt plate 212 may be larger than a diameter of the central aperture 402 of the mounting plate 208 to accommodate concentric positioning of the bushing 420 around an outer surface of the steel tube 222 and the tilt plate 212 around the bushing 420 and the steel tube 222. The mounting plate 208 is thereby coupled to the tilt plate 212 by the steel tube 222. The mounting plate 208 is spaced away from the tilt plate 212 by the first needle bearing stack 418 to minimize friction between surfaces of the mounting plate 208 and the tilt plate 212 that may otherwise oppose rotational movement of the mounting plate 208. The bushing 420 allows the steel tube 222 to rotate within the central aperture 422 of the tilt plate 212.

A second needle bearing stack 423, also formed from three annular disks, is positioned behind the tilt plate 212 and between the tilt plate 212 and a set of wave springs 424. The set of the wave springs 424 depicted in FIG. 4 includes 3 individual wave springs but in other examples, more or less wave springs 424 may be included in the set of wave springs 424 to provide a suitable amount of spring force along an axial direction (e.g., along the central axis 220), to minimize space between components of the head 204 circumferentially surrounding the steel tube 222, as shown in FIG. 3, and stacked along the central axis 220. In this way, when the head 204 is tilted via the friction hinges 232 along the direction indicated by arrow 256 in FIG. 4, the components of the head 204 move together as a single unit.

A snap ring 426 is disposed behind the set of wave springs 424. The snap ring 426 may be configured to be tightened around the steel tube to act as a brace to secure and maintain the stacked components of the head 204 in place around the steel tube 222. The snap ring 426 may be compressed in place by a tool such as pliers or vice grips and, once compressed, may not be readily removed. The snap ring 426 may resist the spring force imposed by the set of wave springs 424, causing the components in front of the set of wave springs 424 to absorb the spring force.

The components of the head 204 of the tablet arm 202 may further include a plurality of bolts oriented both parallel with the central axis 220, e.g., the bolts 236, and perpendicular to the central axis 220, e.g., the plurality of bolts 428. The plurality of bolts may align with apertures in one or more of the stacked components, allowing components to be coupled to form a cohesive unit. For example, a first bolt 430 of the bolts 236, the first bolt 430 parallel with the central axis 220, may be threaded through an aperture in the first section 250 of one of the friction hinges 232, through an aperture in one of the standoff blocks 226, and into an aperture in the tilt plate 212, the apertures all linearly aligned. As another example, a second bolt 432 of the plurality of bolts 428, the second bolt 432 arranged perpendicular to the central axis 220, may be inserted through an aperture in the second section 252 of one of the friction hinges 232 and into an aperture in the shelf 278 at the top end 238 of the stem 206. The apertures may be linearly aligned along the y-axis and insertion of the second bolt 432 secures the head 204 of the tablet arm 202 to the stem 206.

In this way, the tablet arm 202 may be configured to allow rotation at the mounting plate 208, relative to the stem 206, and enable tilting of the head 204 relative to the stem 206 via the friction hinges 232. The mounting plate 208 may be locked into two positions, the two positions arranged perpendicular to one another, by engagement of the ball spring plungers 224 with the plurality of pockets in the rear-facing surface of the mounting plate 208. Rotational movement of the mounting plate 208 may be bound by interaction of the stop pin 410, protruding in the forwards direction from the tilt plate 212, with the curved slot 404 in the mounting plate 208. It will be appreciated that the tablet arm 202 depicted in FIGS. 2-4 is a non-limiting example and variations in shape, dimensions, number of components, angles of rotation and tilt, are possible without departing from the scope of the present disclosure.

The tablet arm 202 may also contain and guide cables coupled to cable ports in a rear-facing surface of the tablet device. The cable ports may be aligned with the central axis 220 and with the central apertures of the stacked components of the head 204 of the tablet arm 202, including the central aperture 402 of the mounting plate 208 and the central aperture 422 of the tilt plate 212. The cables coupled to the cable ports may protrude from the rear-facing surface of the tablet device along the central axis 220, through the steel tube 222. To maintain organization of the cables and inhibit contact of the cables with external objects, the cables may be fed through the tablet arm 202 and enclosed within the interior of the tablet arm 202 between the tablet device and the outer housing of the bearing assembly.

For example, a path of the cables through the tablet arm 202 is indicated by arrows 302 in FIG. 3. The cables may extend into the head 204 of the tablet arm 202 from the tablet device, thread through the opening 403 in the shelf 278 of the top end 238 of the stem 206, as shown in FIG. 4, and continue down through the interior of the stem 206. The cables may extend though an opening in the circular base 262 that is aligned with a port in the outer housing of the bearing assembly to enable the cables to couple to other devices of the mobile x-ray imaging system, such as a power source, motors adjusting a position of a C-arm gantry, an x-ray source, etc.

The cables may be bundled into a cable bundle by securing the cables together with a zip-tie at an end of the cable bundle proximate to the cable ports of the tablet device. The zip-tie may also attached the cable bundle to the tail 260 of the cable zip-tie clip 258 in the steel tube 222. A bundling of cables and securing of the cables to a cable zip-tie clip is shown in FIGS. 8 and 9. Therein, a rear perspective view of a tablet device 802, which may be the tablet device 140 of FIG. 1, is shown in FIG. 8 in a first position 800 where the tablet device 802 is positioned in a landscape orientation. A similar rear perspective view of the tablet device 802 is shown in FIG. 9 in a second position 900 where the tablet device 802 is positioned in a portrait orientation, the second position 900 perpendicular to the first position 800. A head 803 of a tablet arm 805 is depicted in FIGS. 8 and 9 with a top cover of the head 803 removed to show inner components of the head 803. In one example, the head 803 and the tablet arm 805 may be used similarly as the head 204 and the tablet arm 202 of FIGS. 2-4.

A bundle of cables 804 protrudes from a rear-facing surface 806 of the tablet device 802, through a steel tube 808. The cable bundle 804 may be bundled together by a zip-tie 810 that is also looped around a cable zip-tie clip 812. The cable zip-tie clip 812 may be attached to an inner surface of the steel tube 808. As a result, the steel tube 808, cable zip-tie clip 812, and cable bundle 804 may rotate together when the tablet device 802 is adjusted between the first position 800 and the second position 900.

The tablet device 802 may be coupled to a mounting plate 814, which may be the mounting plate 208 of FIGS. 2-4 in some examples. The mounting plate 814 may be attached to the tablet device 802 so that the rear-facing surface 806 of the tablet device is in face-sharing contact with a front-facing surface of the mounting plate 814. The tablet device 802 may be mounted to the mounting plate 814 by a plurality of fasteners 816, such as bolts or screws. In some examples, the tablet device 802 may be connected to the mounting plate 814 by quick-release connectors that allow rapid disconnection of the tablet device 802 from the mounting plate 814 without additional tools. The mounting plate 814 is rotatably coupled to a tilt plate 818, which, in some examples, may be the tilt plate 212 of FIGS. 2-4, via a stack of components as described above with reference to FIGS. 2-4. The mounting plate 814 is configured to rotate 90 degrees clockwise relative to the tilt plate 818 and the tablet arm 805.

When the tablet device 802 is manually adjusted, e.g., pressure applied by an operator's hand, from the first position 800 to the second position 900, the tablet device 802, the mounting plate 814, the steel tube 808, and the cable zip-tie clip 812 move in unison. As the cable bundle 804 is coupled to cable ports in the rear-facing surface 806 of the tablet device 802, the cable bundle 804 also rotates by 90 degrees in the clockwise direction from the first position 800 to the second position 900. The cable bundle 804 extends along a central axis of rotation 820 of the head 803 of the tablet arm 805, attached to the cable zip-tie clip 812 by the zip-tie 810. The 90 degree rotation of the tablet device causes the cable bundle 804 to spin or twist clockwise by 90 degrees rather than sweeping through an arc if the cable bundle 804 were coupled to the tablet device at a distance away from the central axis of rotation 820. A torque exerted on a connecting point between the cable bundle 804 and the rear-facing surface 806 of the tablet device 802, e.g., at the cable ports, may be much smaller than if the cables are instead coupled to the tablet device at a region away from the central axis of rotation 820, such as along an outer periphery of the tablet device 802.

Attachment of the cable bundle 804 to the cable zip-tie clip 812 allows the cable bundle 804 to remain untangled during rotation and to suspend the cable bundle 804 above any components of the head 803 of the tablet arm 805 that may come into contact with the cable bundle 804. Over time, friction generated between the cable bundle 804 and components in contact with the cable bundle 804 during rotational movement of the cable bundle 804 may degrade coatings or sleeves surrounding cables of the cable bundle 804. The transmission of the twisting of the cable bundle 804 from the end coupled to the tablet device 802 along a length of the cable bundle may decay rapidly along the length. As such, a portion of the cable bundle 804 extending through a stem 807 of the tablet arm 805 may experience little motion.

Figure 11:
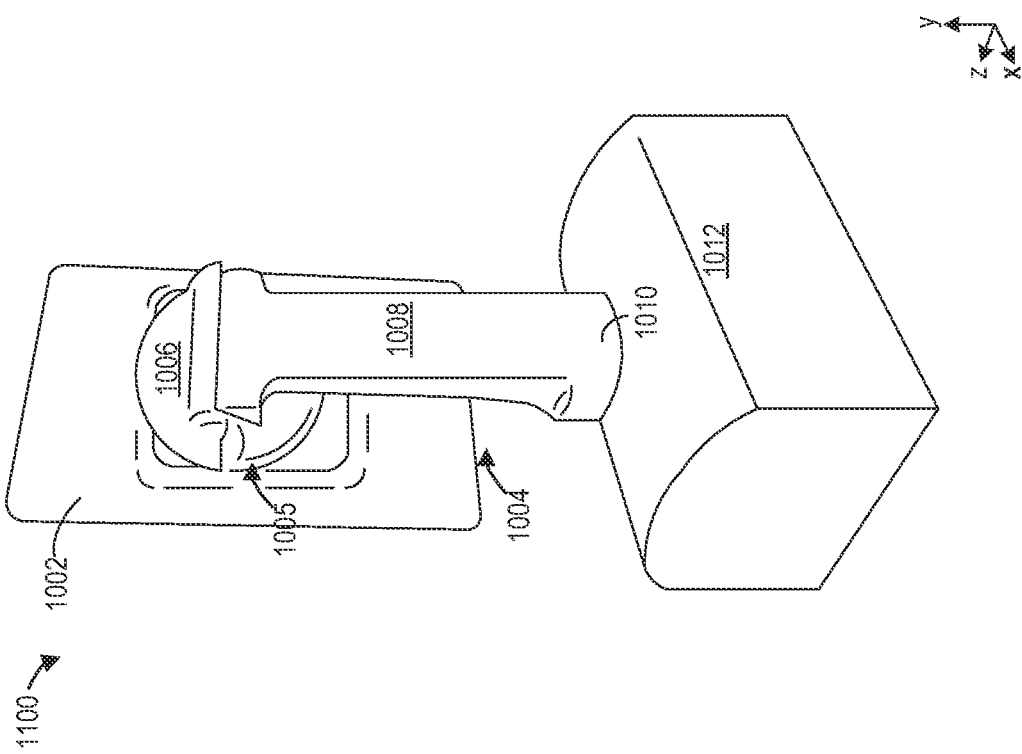
FIG. 11 shows the example of the arm coupled to the tablet device with the tablet device in a portrait orientation, from the rear perspective view of the tablet device.
Figure 10:
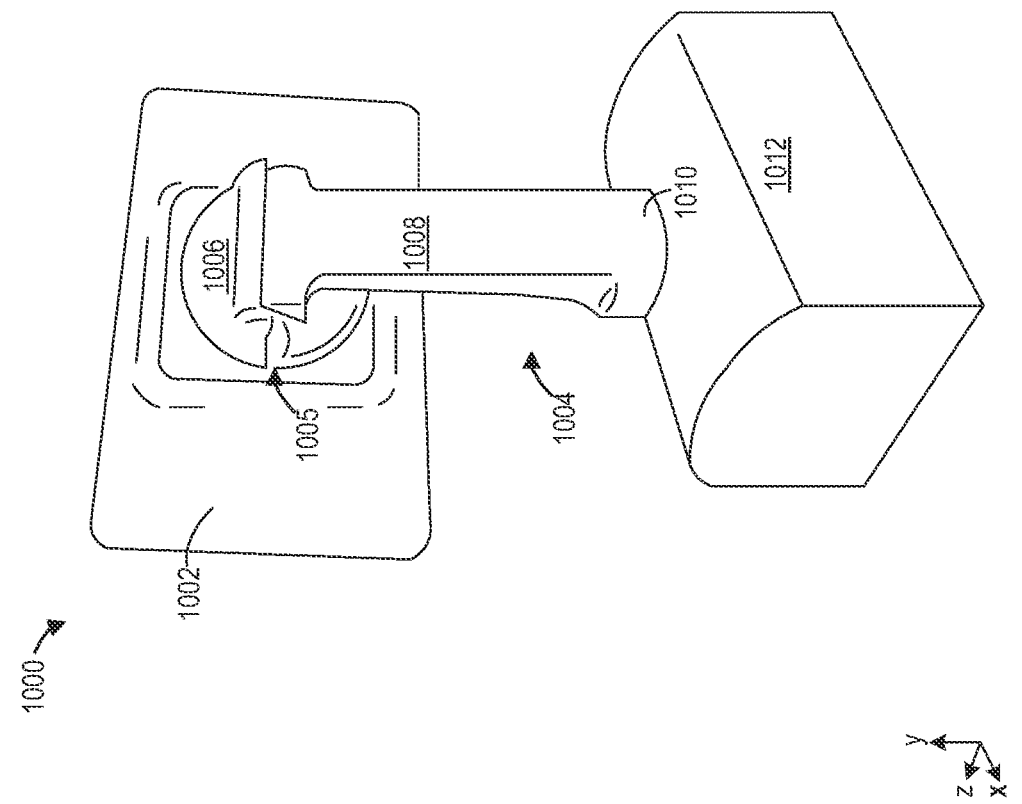
FIG. 10 shows an example of an arm coupled to a tablet with the tablet device in a landscape orientation, from a rear perspective view of the tablet device.
Figure 12:
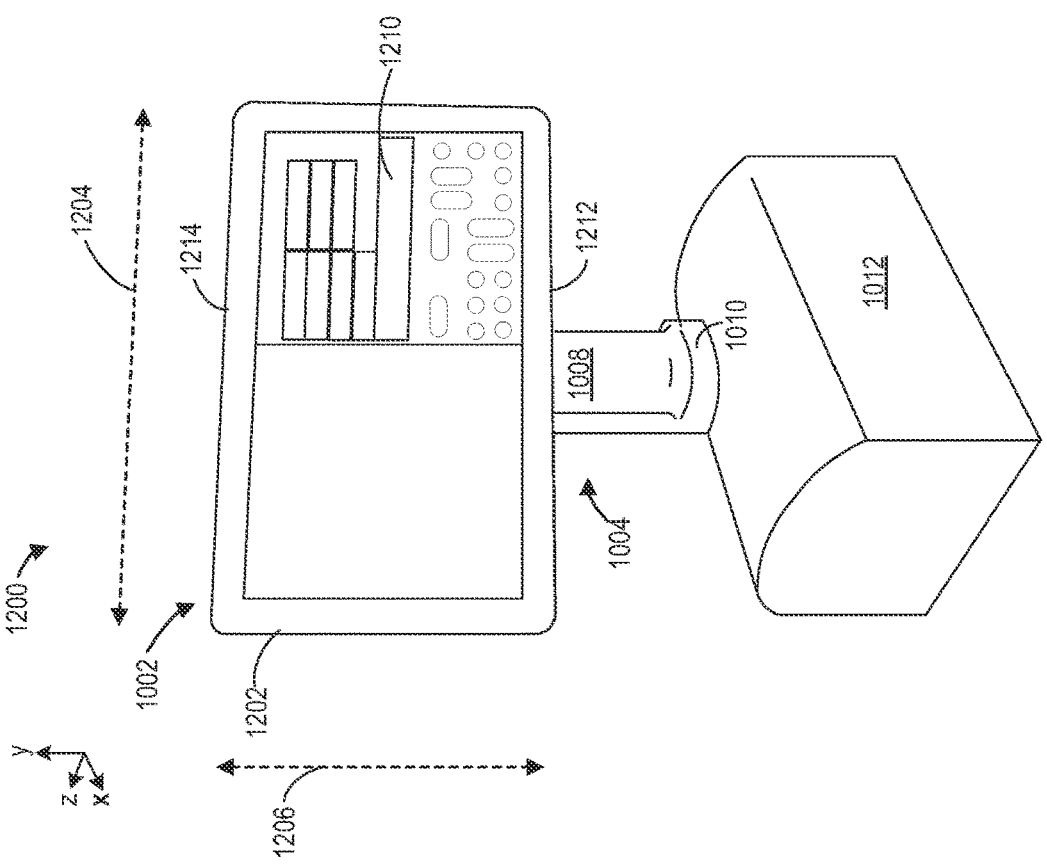
FIG. 12 shows the example of the arm coupled to the tablet device with the tablet device in the landscape orientation, from a front perspective view of the tablet device.

A cable bundle extending along an axis of rotation from a rear-facing surface of a tablet device may be further shielded from external objects by attached a top cover over a head of a tablet arm, as shown in FIGS. 10-11. A tablet device 1002 is shown from a perspective view in a first position 1000 in FIG. 10, positioned in a landscape orientation. The tablet device 1002 is pivoted to a second position 1100 in FIG. 11, positioned in a portrait orientation. In both FIGS. 10 and 11, the tablet device 1002 is mounted on a tablet arm 1004 that includes a head 1006 and a stem 1008. The tablet arm 1004 is coupled at a circular base 1010 of the stem 1008 to an outer housing of a bearing assembly 1012 positioned below the tablet arm 1004, with respect to the y-axis.

The tablet device 1002 and tablet arm 1004 are also shown in FIGS. 12 and 13, with the tablet arm 1004 swiveled by 180 degrees so that a front side of the tablet device 1002 and tablet arm 1004 are depicted. The stem 1008 of the tablet arm 1004 includes a front cover in FIGS. 12-13, and application of both the front cover and the top cover of the head 1006 of the tablet arm 1004 completely encloses cables of the tablet device 1002 and hide the cables from view. By encapsulating the cables within the tablet arm 1004, an organization of the cables as well as an aesthetic appeal is maintained and sterilization of a mobile x-ray imaging system incorporating the tablet arm 1004 and tablet device 1002 is simplified.

Returning to FIGS. 10 and 11, the head 1006 of the tablet arm 1004 may include an outer housing 1005, the outer housing 1005 including the top cover of the head 1006, that fully encloses inner components of the head 1006, such as a mounting plate, a tilt plate, springs, friction hinges, a cable bundle, etc. The outer housing 1005 of the head 1006 may shield the inner components from contact with external objects in all directions, impede entry of particulate matter, such as dust, and maintain an aesthetic quality of the tablet arm 1004. As the tablet device 1002 is adjusted between the first position 1000 and the second position 1100, the outer housing 1005 of the head 1006 remains stationary, the mounting plate rotating within the outer housing 1005 of the head 1006. The outer housing 1005 of the head 1006 may be coupled to the head 1006 so that the outer housing 1005 is spaced slightly away from a rear-facing surface of the tablet device 1002. Thus the outer housing of the head 1006 does not impede rotation of the tablet device 1002 by generating friction against the rear-facing surface of the tablet device 1002.

The tablet device 1002, tablet arm 1004, and outer housing of the bearing assembly 1012 are shown in FIGS. 12-13 from the same perspective as in FIGS. 10-11. However, the tablet arm 1004 is swiveled about a connection point of the circular base 1010 of the stem 1008 to the outer housing of the bearing assembly 1012 so that a display screen 1202 of the tablet device 1002 is depicted. A first position 1200 of the tablet device 1002 shown in FIG. 12 depicts the tablet device 1002 swiveled 180 degrees relative to the first position 1000 of FIG. 10. Similarly, a second position 1300 of the tablet device 1002 shown in FIG. 13 depicts the tablet device 1002 swiveled 180 degrees relative to the second position 1100 of FIG. 11.

In the first position 1200 of FIG. 12, the tablet device 1002 is in the landscape orientation with a first width 1204 of the tablet device 1002 greater than a first height 1206 of the tablet device 1002. The display screen 1202 is divided into two portions: a reference image 1208 on a left-hand portion and a control panel 1210 on a right-hand portion. The reference image 1208 may be an x-ray image obtained from a patient positioned at an isocenter of a C-arm gantry of a mobile x-ray imaging system, with reference to the mobile x-ray imaging system 100 of FIG. 1. An x-ray detector of the mobile x-ray imaging system may transmit information to a system controller that converts the information into the x-ray image displayed on the display screen 1202.

The control panel 1210 adjacent to the reference image 1208 may rely on a touch-sensitive capacity of the display screen 1202 to allow an operator to control the mobile x-ray imaging system. In a conventional x-ray imaging system, a physical control panel may be positioned along an outer housing of a bearing assembly, e.g., the outer housing of the bearing assembly 116 of FIG. 1. The control panel 1210 displayed on the display screen 1202 may closely replicate the physical control panel, adapted with a similar arrangement of buttons, switches, and/or dials to mimic the conventional control panel. The control panel 1210 displayed on the display screen 1202, however, relies on touch-sensitivity to activate the buttons, switches, and/or dials of the control panel 1210.

The two portions of the display screen 1202 are arranged side-by-side in the landscape orientation to maximize dimensions of each displayed portion across a surface area of the display screen 1202. By displaying the two portions in line along a horizontal axis of the display screen 1202, e.g., perpendicular to gravity, an operator may have a clear view of the reference image 1208 while easily accessing the control panel 1210.

When the tablet device 1002 is rotated to the second position 1300 in FIG. 13, the dimensions of the tablet device 1002 are switched so that a second height 1306, equivalent to the first width 1204, is greater than a second width 1304, equivalent to the first height 1206, of the tablet device 1002. In the portrait orientation, a bottom edge 1308 of the tablet device 1002, shown in FIG. 13, is lower (with respect to the y-axis) than a bottom edge 1212 of the tablet device 1002, shown in FIG. 12, when the tablet device is in the landscape orientation. A height, defined along the y-axis, of the tablet arm 1004 may be adapted to accommodate the second height 1306 of the tablet device 1002 in the second position 1300 so that the bottom edge 1308 of the tablet device 1002 does not extend below the circular base 1010 of the tablet arm 1004.

An upper edge 1310 of the tablet device 1002, shown in FIG. 13, is also higher than an upper edge 1214 of the tablet device 1002, shown in FIG. 12, when the tablet device 1002 is in the portrait orientation compared to the landscape orientation. Furthermore, images displayed on the display screen 1202 may automatically be re-positioned when the tablet device 1002 is rotated between the first position 1200 and the second position 1300.

In the portrait orientation, the display screen 1202 of the tablet device 1002 also includes two portions; an upper portion displaying a reference image 1312, similar to the reference image 1208 of FIG. 12, and a lower portion displaying a control panel 1314, similar to the control panel 1210 of FIG. 12. The two portions are stacked vertically, along the y-axis to maximize a display area of each portion. By positioning the control panel 1314 below the reference image 1312, the control panel 1314 in the second position 1300 is lower, along the y-axis, than the control panel 1210 in the first position 1200 by a distance 1316, relative to an operator standing adjacent to the tablet device 1002.

Although the control panel 1314 is stacked below the reference image 1312 instead of beside the reference image 1312, as for the first position 1200 of FIG. 12, the control panel 1314 is arranged identical to the control panel 1210 in FIG. 12. An orientation and alignment of the buttons, switches, and/or dials are retained regardless of the orientation of the tablet device 1002. However, a positioning of the reference image 1312 and the control panel 1314 may be shifted along the y-axis in the second position 1300 relative to the first position 1200 of FIG. 12.

For example, adjustment of the tablet device 1002 to the portrait orientation may be desirable for an operator of shorter stature. The lower placement of the control panel 1314 in the portrait orientation shown in FIG. 13 may allow the shorter operator to access the control panel more comfortably, particularly during prolonged periods of operation of the mobile x-ray imaging system. Pivoting the tablet device 1002 between the landscape and portrait orientations while maintaining coupling of the tablet device 1002 to the tablet arm 1004 and maintaining attachment of cables to a rear surface of the tablet device 1002 allows the mounted tablet device 1002 to efficiently accommodate operators of various heights.

In this way, a tablet arm enables a tablet device to be tilted and swiveled so that the display screen 1202 may be seen from a wide viewing field and the tablet device may be easily adjusted to a more narrow configuration (e.g., the portrait orientation) to reduce obstruction of an operator's view of a patient or staff member positioned proximate to an x-ray source of the mobile x-ray imaging system. The tablet arm is configured to lock the tablet device in a landscape or a portrait orientation, with a reference image and control panel displayed on the tablet device automatically repositioned based on the orientation of the tablet device. Adjustment of the orientation of the tablet device is conducted without decoupling cables from the tablet device resulting from a connection of the cables along an axis of rotation of the tablet device, thereby reducing torque imposed on the cable connections. The tablet device may be readily dismounted from the tablet arm and detached from the cables to be utilized as a portable, wireless device.

FIGS. 1-15 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

A technical effect of the disclosure includes adjustment of a mounted tablet device between a landscape and a portrait orientation by a tablet arm with a mobile joint. Another technical effect of the disclosure includes minimizing torque imposed on cables attached to the mounted tablet by coupling the cables to a rear surface of the tablet device along an axis of rotation of the tablet device.

In one embodiment a tablet arm includes an upper portion configured to rotate a mounted electronic device relative to a central axis of the upper portion and a lower portion coupled to the upper portion and extending downwards, away from the upper portion along a vertical axis perpendicular to the central axis, the upper portion and lower portion forming a hollow structure configured to house cables of an electronic device. In a first example of the tablet arm, the upper portion includes a mounting plate configured to couple to a rear-facing surface of the electronic device. A second example of the tablet arm optionally includes the first example, and further includes wherein the mounting plate is configured to rotate 90 degrees around the central axis of the upper portion. A third example of the tablet arm optionally includes one or more of the first and second examples, and further includes, wherein the upper portion includes a tilt plate arranged behind the mounting plate and spaced away from the mounting plate by a plurality of annular components of the upper portion. A fourth example of the tablet arm optionally includes one or more of the first through third examples, and further includes, wherein the tilt plate has ball spring plungers configured to engage with pockets in the mounting plate and lock the mounting plate in of two positions, the mounting plate rotatable between the two positions. A fifth example of the tablet arm optionally includes one or more of the first through fourth examples, and further includes, wherein the tilt plate has a top pin protruding from a front-facing surface of the tilt plate that extends through a curved slot in the mounting plate. A sixth example of the tablet arm optionally includes one or more of the first through fifth examples, and further includes, wherein rotation of the mounting plate through 90 degrees is halted in a first direction by contact between the top pin and a first end of the curved slot and halted in a second direction, the second direction opposite of the first direction, by contact between the top pin and a second end of the curved slot. A seventh example of the tablet arm optionally includes one or more of the first through sixth examples, and further includes, wherein the tilt plate and the mounting plate are similarly coupled to a steel tube extending through central apertures of both the tilt plate and the mounting plate. An eighth example of the tablet arm optionally includes one or more of the first through seventh examples, and further includes, wherein the upper portion includes friction hinges configured to pivot the upper portion relative to the vertical axis and maintain a tilted position of the upper portion.

In another embodiment, a mounting system for a medical imaging device includes a tablet arm configured to enclose cables coupled to the medical imaging device, the tablet arm including, a tiltable and pivotable head arranged at an upper end of the tablet arm configured to couple to a rear-facing surface of the medical imaging device, and a stem extending vertically down from the head. In a first example of the mounting system, the head and the medical imaging device are configured to pivot through 90 degrees relative to a central axis of the head as a single unit. A second example of the mounting system optionally includes the first example, and further includes, wherein the head is configured to lock the medical imaging device in a first position that corresponds to a landscape orientation of the medical imaging device and a second position that corresponds to a portrait orientation of the medical imaging device. A third example of the mounting system optionally includes one or more of the first and second examples, and further includes, wherein the head is configured to unlock the tablet from the first position and the second position when a force is applied to the medical imaging device along a radial direction around the central axis of the head. A fourth example of the mounting system optionally includes one or more of the first through third examples, and further includes, wherein the head and the stem have hollow interiors that are fluidly coupled by an opening in a shelf of the head. A fifth example of the mounting system optionally includes one or more of the first through fourth examples, and further includes, wherein the hollow interiors of the head and the stem are configured to accept and guide cables connected to the rear-facing surface of the medical imaging device along the central axis of rotation of the head and down through the stem continuously. A sixth example of the mounting system optionally includes one or more of the first through fifth examples, and further includes, wherein the cables are attached to a clip arranged in the head of tablet arm in a path of the cables by a zip-tie. A seventh example of the mounting system optionally includes one or more of the first through sixth examples, and further includes, wherein the cables at a connecting point between the cables and medical imaging device are configured to twist along the central axis of rotation when the medical imaging device is pivoted between the portrait and landscape orientations.

In another embodiment, a display for an x-ray imaging system includes a hollow arm for mounting a display device, the arm including a first portion configured to rotate and a second, stationary portion and a display device with cable ports on a rear-facing surface and coupled to the first portion of the hollow arm. In a first example of the display, cables of the display device protrude from a central region of the display device along a central axis of rotation and extending through an interior of the hollow arm hidden from view. A second example of the display optionally includes the first example, and further includes, wherein the display device is configured to be quickly disconnected from the first portion of the hollow arm without use of additional tools.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A tablet arm comprising:
   an upper portion configured to rotate a mounted electronic device relative to a central axis of the upper portion; and
   a lower portion coupled to the upper portion and extending downwards, away from the upper portion along a vertical axis perpendicular to the central axis, the upper portion and lower portion forming a hollow structure configured to house cables of an electronic device,
   wherein the upper portion includes a tilt plate, a set of standoff blocks, and friction hinges, and wherein a first end of the set of standoff blocks is coupled to a rear-facing surface of the tilt plate, and a second end of the set of standoff blocks is attached to the friction hinges, the first end and the second end arranged on opposite surfaces of the set of standoff blocks.

2. The tablet arm of claim 1, wherein the upper portion includes a mounting plate configured to couple to a rear-facing surface of the electronic device.

3. The tablet arm of claim 2, wherein the mounting plate is configured to rotate 90 degrees around the central axis of the upper portion.

4. The tablet arm of claim 3, wherein the tilt plate arranged behind the mounting plate and spaced away from the mounting plate by a plurality of annular components of the upper portion.

5. The tablet arm of claim 4, wherein the tilt plate has ball spring plungers configured to engage with pockets in the mounting plate and lock the mounting plate in of two positions, the mounting plate rotatable between the two positions.

6. The tablet arm of claim 4, wherein the tilt plate has a top pin protruding from a front-facing surface of the tilt plate that extends through a curved slot in the mounting plate.

7. The tablet arm of claim 6, wherein rotation of the mounting plate through 90 degrees is halted in a first direction by contact between the top pin and a first end of the curved slot and halted in a second direction, the second direction opposite of the first direction, by contact between the top pin and a second end of the curved slot.

8. The tablet arm of claim 4, wherein the tilt plate and the mounting plate are similarly coupled to a steel tube extending through central apertures of both the tilt plate and the mounting plate.

9. The tablet arm of claim 1, wherein the upper portion includes friction hinges configured to pivot the upper portion relative to the vertical axis and maintain a tilted position of the upper portion, and wherein the friction hinges include three sections: a first section coupling directly to the set of standoff blocks, a second section, and a third section coupling directly to a top end of the lower portion.

10. A mounting system for a tablet, comprising:
a tablet arm configured to enclose cables coupled to the tablet, the tablet arm including:
a tiltable and pivotable head arranged at an upper end of the tablet arm configured to couple to a rear-facing surface of the tablet; and
a stem extending vertically down from the head,
wherein the upper end of the tablet arm includes a tilt plate, a set of standoff blocks, and friction hinges, and wherein a first end of the set of standoff blocks is coupled to a rear-facing surface of the tilt plate, and a second end of the set of standoff blocks is attached to the friction hinges, the first end and the second end arranged on opposite surfaces of the set of standoff blocks.

11. The mounting system of claim 10, wherein the head and the tablet are configured to pivot through 90 degrees relative to a central axis of the head as a single unit.

12. The mounting system of claim 11, wherein the head is configured to lock the tablet in a first position that corresponds to a landscape orientation of the tablet and a second position that corresponds to a portrait orientation of the tablet.

13. The mounting system of claim 12, wherein the head is configured to unlock the tablet from the first position and the second position when a force is applied to the tablet along a radial direction around the central axis of the head.

14. The mounting system of claim 10, wherein the head and the stem have hollow interiors that are fluidly coupled by an opening in a shelf of the head.

15. The mounting system of claim 14, wherein the hollow interiors of the head and the stem are configured to accept and guide cables connected to the rear-facing surface of the tablet along the central axis of rotation of the head and down through the stem continuously.

16. The mounting system of claim 15, wherein the cables are attached to a clip arranged in the head of tablet arm in a path of the cables by a zip-tie.

17. The mounting system of claim 12, wherein the cables at a connecting point between the cables and tablet are configured to twist along the central axis of rotation when the tablet is pivoted between the portrait and landscape orientations.

* * * * *